United States Patent
Hoppe et al.

(10) Patent No.: US 7,067,292 B2
(45) Date of Patent: Jun. 27, 2006

(54) METHOD FOR THE PRODUCTION OF PHOSPHOLIPIDS

(75) Inventors: Hans-Ulrich Hoppe, Freising (DE);
Dirk Bökenkamp, Freising (DE);
Sinian Huang, Freising (DE)

(73) Assignee: Bioghurt Biogarde GmbH & Co. KG, Freising (DE)

( * ) Notice: Subject to any disclaimer, the term of this patent is extended or adjusted under 35 U.S.C. 154(b) by 108 days.

(21) Appl. No.: 10/488,143

(22) PCT Filed: Aug. 28, 2002

(86) PCT No.: PCT/EP02/09611

§ 371 (c)(1),
(2), (4) Date: Feb. 26, 2004

(87) PCT Pub. No.: WO03/020941

PCT Pub. Date: Mar. 13, 2003

(65) Prior Publication Data
US 2004/0235119 A1    Nov. 25, 2004

(30) Foreign Application Priority Data
Aug. 28, 2001   (DE) ............................... 101 42 014

(51) Int. Cl.
*C12P 7/64*    (2006.01)
(52) U.S. Cl. ...................... 435/134; 435/135; 435/136
(58) Field of Classification Search ...................... None
See application file for complete search history.

(56) References Cited

U.S. PATENT DOCUMENTS 5,183,750 A * 2/1993 Nishide et al. ............. 435/134

FOREIGN PATENT DOCUMENTS

| | | |
|---|---|---|
| CA | 2 055 990 A | 5/1992 |
| DE | 199 17 249 A | 9/2000 |
| EP | 0 285 421 A | 10/1988 |
| EP | 0 399 544 A | 11/1990 |
| EP | 1 223 222 A | 7/2002 |
| EP | 1 231 213 A | 8/2002 |
| GB | 1 581 810 A | 12/1980 |
| JP | 04 267882 A | 9/1992 |
| JP | 05336984 A2 | 12/1993 |
| WO | WO 91 16444 A | 10/1991 |
| WO | WO 00 77183 A | 12/2000 |

OTHER PUBLICATIONS

The Terms "stage" and "derive" Merriam-Webster Online Dictionary. se at the web at http://www.m-w.com. p. 1 and 2.*
Uesugi Y. et al. "Recognition of phospholipids in Streptomyces phospholipase D". J. Biol. Chem., Jul. 2005, 280(28): 26143-26151. see pp. 26143-26144 and Fig. 1, in particular.*
Juneja LR et al. "Conversion of phosphatidylcholine to phosphatidylserine by various phospholipase D in the presence of L- or D-serine". Biochem. et Biophys. Acta, 1989, 1003: 277-283. entire document.*
Properties of Phospholpase D. From . . . Sativus, Rakhimov, et al. Biochemistry Consultants Bureau, NY, Feb. 1981.
Patent Abstracts of Japan, vol. 017, Feb. 23, 1993.
Phosphatidylglycerol preparation from Soy . . . D, Yakugaku, Journ. of the Japan Oil Chem. Soc., vol. 42.
Derwent-Abstract No. 1986-275 060/423.
Chemical Abstracts Nr. 120: 215 491.
Derwent-Abstract Nr. 1988 333 494/47—Mar. 31, 1987.

* cited by examiner

*Primary Examiner*—Sandy E. Saucier
*Assistant Examiner*—Satyendra K. Singh
(74) *Attorney, Agent, or Firm*—Fulbright & Jaworski L.L.P.

(57) ABSTRACT

The invention relates to a method for the production of phospholipids of general formula (I) with the exclusive aid of phospholipase D from a phospholipid mixture and without using organic solvents, wherein phosphatidyl acid is produced in an aqueous, unbuffered phase with phospholipase D and at least one bivalent metal ion in a first step and at least one phospholipid of general formula (I) is produced from the phosphatidyl acid having at least one compound of general formula (II) $R^3$—OH in a second step. Phosphatidylserine, phosphatidylcholine, phosphatidylethanolamine, phosphatidylinosite and/or phosphatidylglycerine are obtained as products. In another embodiment of the invention, the PLD is identical or different in both steps of said method, wherein in the latter case the pH values for the first and second steps of the method are different, said values lying particularly between 6.5 and 8.0, especially between 5.0 and 7.5. The novel method makes it possible to easily obtain products with high yields and excellent purity thereby rendering said products suitable for applications in the food industry and pharmaceutical applications.

22 Claims, No Drawings

METHOD FOR THE PRODUCTION OF PHOSPHOLIPIDS

This is a §371 of PCT/EP02/09611 filed Aug. 28, 2002, which claims priority from German 101 42 014.5 filed Aug. 28, 2001, each of which are hereby incorporated by reference in their entireties.

The present invention relates to a method for the production of phospholipids.

Phospholipids, also referred to as lecithins, such as, for example, soybean and egg yolk lecithins, have long been used in food products, cosmetic products, paints, lubricants, magnetic materials, animal feeds and medicinal and agrochemical products. In this connection, phosphatidyl acid derivatives produced by enzymatic transphosphatidylation from phospholipids and compounds containing hydroxyl groups in some cases show properties superior to those of the starting material.

Phospholipase D (PLD) is employed in particular for the hydrolytic production of phosphatidyl acid in the presence of water and, when a divalent metal ion is simultaneously present, it is possible for phosphatidyl radicals to be transferred to an alcoholic compound having hydroxyl groups as acceptor.

The presence of divalent metal ions is indispensable for phospholipases D to show corresponding transphosphatidylation activities. Only in transphosphatidylation reactions between identical phospholipid molecules or phosphatidylglycerol have corresponding activities also been detected in the absence of divalent metal ions.

Care must therefore be taken, especially in transphosphatidylation reactions between different phospholipid molecules, that the reaction system contains no substances which react with these divalent ions, nor that compounds which contain hydroxyl groups and which lose their corresponding reactivity under the influence of divalent ions are employed.

Care must furthermore be taken that, for example, in the pH range between 5 and 8 which is mostly employed for PLD reactions, no buffers which precipitate with divalent ions, and in particular calcium ions, are used.

Numerous documents describing methods for the production of phospholipids using PLD are known from the literature.

These are mostly dominated by two-phase systems consisting of an aqueous and an organic phase, because phospholipids have, as natural main constituents of biomembranes, amphiphilic properties.

Although PLD is also capable of a transesterification reaction in above-stoichiometric amounts of water, typically organic solvents or detergents are employed, because the lipid substrates used are insoluble in water, and only poor conversion by the enzyme of the lipids is possible in the form of aqueous liposomal dispersions.

Two-phase systems thus represent the prior art, the enzyme being soluble in the aqueous phase and the supplied lipid being soluble in the organic solvent; the enzymatic reaction proceeds at the phase boundary between water and the organic phase.

Since the use of detergents or organic solvents may be associated with problems especially in relation to the production of pharmaceutical products or food products, and the hydrolysis product phosphatidyl acid, which is not always desired, results under the two-phase conditions mentioned, possible ways of carrying out PLD-catalyzed transesterification processes also in a purely aqueous phase have been sought.

Thus, WO 00/77183 discloses a corresponding method for the enzyme-catalyzed transesterification or hydrolysis of phospholipids, in which the enzyme (phospholipase D inter alia) is dissolved in an aqueous medium which contains a liposomal suspension of phospholipids, water, an alcohol or an alcohol derivative as hydroxyl-carrying component and, if necessary, a divalent metal cation. A silica gel is then added to the aqueous medium, and the mixture resulting therefrom is stirred.

The enzymatic production of phosphatidyl acids is described in JP 04267882. In this case, lecithin powders having a specific particle size are homogenized with soybean extracts containing phospholipase C and phospholipase D and then reacted for 24 hours. In this way, approximately 96% of the phospholipids are obtained as phosphatidyl acids.

A method for the production of modified phospholipids is described in EP-B 399 544. According to this, phospholipids are converted with phospholipase D into phosphatidyl acid and a nitrogen-containing base and hydrolyzed with a further enzyme (phospholipase C, phosphodiesterase or an acid phosphatase) to a diglyceride and a phosphorus base, the conversion with the two enzymes preferably taking place simultaneously. Both reaction steps are carried out in a two-phase system consisting of buffer and organic solvent such as an alkyl carboxylate, an alkane, hydrocarbons and others.

M. Kamata et al. [Yukagaku, 1993, 42 (4), 297–301] describe the quantitative conversion of phosphatidylcholin-containing soybean phospholipids to phosphatidyl acid or phosphatidylglycerol with the aid of phospholipase D. In this case, hydrolysis of the phosphatidylcholine to phosphatidyl acid, and the transphosphatidylation of phosphatidylcholine to give phosphatidylglycerol is carried out at pH values of 5.6 and 4.8 respectively. To avert competitive hydrolysis, the pH is adjusted with an acetate buffer.

EP-A 1 223 222 describes a method for exchanging bases on a phospholipid as starting material, in which the phospholipid is exposed to a phospholipase D in the presence of a receptor having hydroxyl groups. In this reaction, which is carried out in an aqueous system, the phospholipid is bound to a carrier material, the receptor component and the phospholipase D are employed in free form.

European patent 285 421 protects a method for the production of a phosphatidic acid derivative by the action of phospholipase D on a phospholipid in the presence of a phosphatidyl radical acceptor. This method is characterized essentially by the step of activating phospholipase D by an organic solvent, which is carried out in the absence of a divalent metal ion and with which the phospholipase D is stimulated to carry out the desired transphosphatidylation reaction.

The particular disadvantage of the described prior art methods is that either the phospholipids employed must be brought into solution in *liposomal form, or else that they must first be bound to appropriate carrier materials before they are used, in order to make them accessible to the PLD.

Although DE-A 199 17 249 describes a method for the production of phosphatidylserine in a purely aqueous single-phase system with the aid of PLD, no detailed statements about the lecithin used, the pH of the reaction, the temperature actually used or else the enzyme source are made, for which reason reproduction is impossible.

Finally, European patent application EP 1 231 213 discloses a method for the production of phosphatides but, although it is carried out both in an exclusively aqueous phase and in the presence of PLD, according to the examples it is absolutely necessary to employ suitable buffers in order to be able to ensure the desired pH conditions.

The object of the present invention was thus to provide a method for the production of phospholipids of the general formula (I)

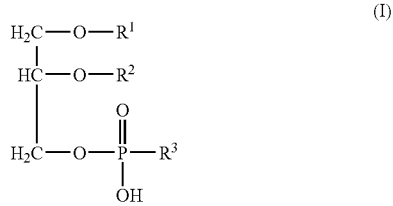

in which

R$^1$ and R$^2$ are independently of one another a saturated, mono- or polyunsaturated C$_{10-30}$-acyl radical, and R$^3$ is

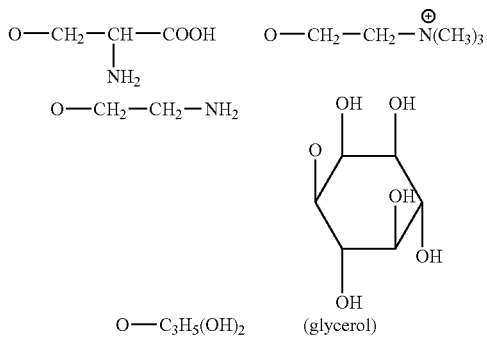

in which the desired products are obtained with the aid of exclusively phospholipase D (PLD) from a phospholipid mixture without using organic solvents.

This object has been achieved by an appropriate method in which in aqueous, unbuffered phase with phospholipase D (PLD) and at least one divalent metal ion phosphatidyl acid (PA) is produced in a first stage, and at least one phospholipid of the general formula (I) is produced in a second stage from phosphatidyl acid with at least one compound of the general formula (II) R$^3$—H, where R$^3$ has the meaning already indicated for formula (I). Suitable compounds of the formula (II) are serine, choline, ethanolamine, inositol and glycerol (bound via one of the three oxygen atoms).

It has surprisingly emerged in practice that the desired phospholipids are obtained in high purity and yield with the process of the invention, which is carried out via the intermediate stage of a phosphatidyl acid, without the need in this case for the phospholipids employed to be subjected to a complicated pretreatment, carrier materials to be removed from the reaction mixture after the reaction has taken place, or of phase-transfer conditions to be maintained.

The present method has proved particularly suitable for the production of phosphatidylserine, phosphatidyl-choline, phosphatidylethanolamine, phosphatidyl-inositol, phosphatidylglycerol or any mixtures thereof, making it additionally advantageous compared with known methods.

The present method is not subject to any restriction in relation to the starting material either, which is why lecithin and here especially soybean, rapeseed oil and/or egg yolk lecithins are recommended as phospholipid mixtures to be regarded as preferred.

Although water is used specifically as reaction medium, surprisingly large amounts of the phospholipid mixture to be employed can be used. In this regard, the invention provides for employing the particular phospholipid mixture in amounts of from 1.0 to 20.0% by weight based on the complete reaction mixture, with corresponding dispersions having proved thoroughly advantageous.

Nor is the PLD subject to any restrictions, but phospholipases D derived from Streptomyces, Actinomadura, peanut, carrot and/or cabbage have proved particularly suitable.

Contrary to the widely held view that the pH optimum for phospholipases is at pH values between 6 and 7, the present method of the invention can be carried out at pH values of the reaction mixture which are between 4.0 and 9.0.

A relatively wide range is also possible for the reaction temperature, and a reaction temperature between 10 to 60° C. is to be regarded as preferred.

Whereas difficulties have repeatedly been reported with the divalent metal ions used from the methods disclosed to date, the method of the invention, which is carried out in a single phase aqueous system, can be carried out in the presence of Ca$^{2+}$, Mg$^{2+}$ and/or Zn$^{2+}$ ions without the occurrence of precipitation reactions, limited enzymic activities or interactions with the employed compound containing OH groups.

The present invention provides preferred metal ion concentration which is between 1.0 and 100 mM.

Particularly good conversion results can be achieved with amounts of PLD which are between 0.1 to 1,000 units/g of phospholipid (mixture) employed.

The fact that the method of the invention can be carried out with extremely few problems is shown by, besides the reaction conditions already mentioned, also the fact that the PLD employed in the first and second stage of the method can be identical, which is why the present invention regards this variant as particularly preferred. In this case, PLD variants derived from Streptomyces species and/or Actinomadura species are particularly suitable.

The present invention also takes account of variants in which the PLD in the two stages of the method are different.

In this case, the present invention provides in a particularly preferred manner PLD derived from Streptomyces chromofuscus, peanut, carrot and/or cabbage to be employed in the first stage of the method. It has likewise proved advantageous in this connection for the pH in the first stage to be between 6.5 and 8.0 and in the second stage of the method to be between 5.0 and 7.5.

Normally, the PLD employed is employed in free form in the purely aqueous reaction medium. However, for certain applications, it may be advantageous for the appropriate PLD or the PLD mixtures employed to be used in immobilized form, in which case covalent and/or adsorptive types of binding are particularly appropriate. Examples of suitable carrier materials for the enzyme are silica gels like those employed in chromatography columns, but also other inert materials with large surface areas such as kieselguhr, activated carbon, bentonites and resins or else three-dimensionally configured adsorbents.

The third component provided according to the invention for the production reaction, the compound of the general formula (II), is not in any way to be regarded as critical either, but it should be employed preferably in concentrations between 0.1 and 5.0 molar.

The preferred reaction time provided according to the invention for the first stage of the method is a period between 5 and 20 hours and for the second stage of the method is a time of from 0.5 to 5 hours.

Although the desired product is obtained in particularly good quality and high purity owing to the simple performance of the method in a single-phase system, it is possible for specific applications or further processings to purify the resulting phospholipid or the mixture containing the latter by an alcoholic extraction, which is likewise taken into account by the present invention.

Overall, the method of the invention provides a particularly environmentally friendly method variant which is simple to carry out and on the basis of which the resulting phospholipid (mixture) can be employed as final product in particular as addition to food products or, for example, else in so-called functional food products without problems and without further processing. In addition, no purification steps at all are necessary in relation to the remaining mother liquor, so that the latter can, with the PLD contained therein, be employed again immediately without regeneration steps.

The following examples illustrate the advantages of the method of the invention for the production of phospholipids.

EXAMPLES

In the following examples, the phospholipid production took place according to the invention in two method stages in a single phase aqueous system in which, in the first step, phosphatidyl acid was produced by the enzymatic hydrolysis of the phospholipid component with PLD and in the presence of $Ca^{2+}$ ions. The reaction temperature was 35 to 60° C., the phospholipase D of microbial origin was employed in amounts which corresponded to 50 to 1,500 units/mM phospholipid, with the pH of the reaction mixture being between 5.5 and 8.0.

In the second step of the method, the reaction conditions were changed from the first step of the method in such a way that L-serine was added as component having OH groups, subsequently in an amount exceeding the employed amount of phospholipid. The pH of the reaction mixture in the second step of the method was between 4.0 and 6.0 and the temperature was 20 to 60° C.

The starting material used was a phospholipid mixture containing phosphatidylcholine, phosphatidylethanolamine and phosphatidylinositol, which was used in amounts of from 15 to 175 mM. Epicuron® 100 P from Lucas Meyer (now Degussa Texturant Systems Deutschland GmbH & Co. KG), consisting of 20 to 25% by weight phosphatidylcholine, 18 to 23% by weight phosphatidylethanolamine and 12 to 15% by weight phosphatidylinositol, and Epicuron® 130 (source: see above), with 30 to 35% by weight phosphatidylcholine, 15 to 20% by weight phosphatidylethanolamine and 8 to 13% by weight phosphatidylinositol have proven to be particularly suitable as starting materials.

The starting material was in each case thoroughly homogenized in the aqueous phase before starting the reaction, and then $Ca^{2+}$ or $Mg^{2+}$ ions were introduced in concentrations of 100 mM.

The PLD used was employed in immobilized form according to Röhm (with use of Eupergit C).

Example 1

1. Firstly a suspension of the phospholipid mixture (2.26 mmol) and $CaCl_2$ (10 mMol) in 100 ml of water was adjusted to pH 6.5 to 7.5 with NaOH (0.1 M). The reaction was then carried out with PLD (1,000 to 1,500 units), stirring at 40° C. for 16 hours. The yield of phosphatidyl acid after 5 hours was 90% of the final value, which was established with the aid of the HPLC method.
2. The phosphatidyl acid obtained in this way was removed from the aqueous phase after the reaction by filtration and washed several times with water, washing out choline, ethanolamine and inositol and salt fractions.
3. The immobilized PLD remained in the precipitate and was used further.
4. The washed phosphatidyl acid (1 to 2 mmol) was then converted further to phosphatidylserine (PS). For this purpose, the solution (10 mM, in water) was first adjusted to pH=5.5 with hydrochloric acid (0.1 mol/l), the temperature was kept at 30° C., and $CaCl_2$ (100 mM) and L-serine in 10-fold excess were added.
5. Then, while stirring, the reaction was allowed to proceed for 10 hours, the yield of PS after 4 hours already being 40% of the final value.
6. After the reaction, the solution was extracted with hexane/isopropanol, and the PS was purified by acetone precipitation.
7. It was possible for the immobilized PLD to be removed, owing to its particle size, using a sieve, and recovered.

Example 2

1. Firstly a suspension of the phospholipid mixture (2.26 mmol) and $CaCl_2$ (10 mmol) in 100 ml of water was adjusted to pH 7 with NaOH (0.1 M). The reaction was then carried out with PLD (1,000 to 1,500 units), stirring at 50° C. for 16 hours. The yield of phosphatidyl acid after 5 hours was 90% of the final value, which was established with the aid of the HPLC method.
2. The phosphatidyl acid obtained in this way was removed from the aqueous phase after the reaction by filtration and washed several times with water, washing out choline, ethanolamine and inositol and salt fractions.
3. It was possible for the immobilized PLD to be separated from PA fractions, owing to its particle size, using a sieve, and recovered.
4. The further steps for producing PS were carried out as in Example 1 (steps 4 to 7).

The invention claimed is:

1. A method for the production of phospholipids of the general formula (I)

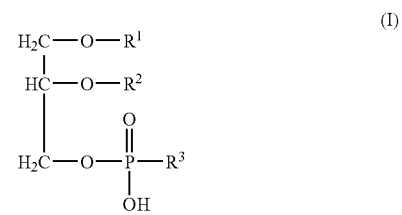

in which $R^1$ and $R^2$ are independently of one another a saturated, mono- or polysaturated $C_{10-30}$-acyl radical, and $R^3$ is

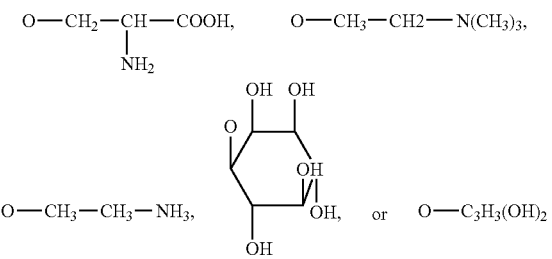

comprising:
- forming a reaction mixture comprising a phospholipid mixture with a phospholipase consisting of phospholipase D (PLD), containing no organic solvents, in an aqueous, unbuffered phase and at least one divalent metal ion, wherein at least one phosphatidyl acid (PA) is produced in a first stage of the reaction;
- isolating the at least one PA produced from the said first stage of the reaction; and
- reacting the at least one PA isolated from said first stage with PLD, and at least one divalent metal ion, and at least one compound of formula (II) $R^3$—H in a second stage of the process, where $R^3$ is as defined for formula (I) and wherein the said compound of formula (II) is only added in said second stage and is not present in said first stage, to produce at least one phospholipid of formula (I).

2. The method as claimed in claim 1, wherein phosphatidylserine, phosphatidylcholine, phosphatidylethanolamine, phosphatidylinositol and/or phosphatidylglycerol are obtained.

3. The method as claimed in claim 1, wherein said phospholipid mixture is lecithin.

4. The method as claimed in claim 1, wherein the phospholipid mixture is employed in amounts of from 1.0% to 20.0% by weight, based on the complete reaction mixture.

5. The method as claimed in claim 1, wherein said PLD is from at least one of *Streptomyces, Actinomyces*, peanut, carrot and cabbage.

6. The method as claimed in claim 1, wherein the pH of the reaction mixture is between 4.0 and 9.0.

7. The method as claimed in claim 1, wherein the temperature of the reaction mixture is from 10° C. to 60° C.

8. The method as claimed in claim 1, wherein said divalent metal ion is selected from the group consisting of $Ca^{2+}$, $Mg^{2+}$ and $Zn^{2+}$.

9. The method as claimed in claim 1, wherein the metal ion concentration is between 1.0 and 100 mM.

10. The method as claimed in claim 1, wherein the PLD is used in amounts of from 0.1 to 1.000 units/g of phospholipid employed.

11. The method as claimed in claim 1, wherein the PLD employed in the first and second stage of the method is identical.

12. The method as claimed in claim 11, wherein the PLD is from at least one of *Streptomyces* species and *Actinomyces* species.

13. The method as claimed in claim 1, wherein the PLD in the two stages of the method is different.

14. The method as claimed in claim 13, wherein in the first stage of the method, PLD is from *Streptomyces chromofuscus*, peanut, carrot and/or cabbage.

15. The method as claimed in claim 13, wherein the pH of the reaction mixture in the first stage is between 6.5 and 8.0, and in the second stage of the reaction is between 5.0 and 7.5.

16. The method as claimed in claim 1, wherein PLD is employed in immobilized form.

17. The method as claimed in claim 1, wherein the compound of the general formula (II) is employed in concentrations between 0.1 and 5.0 molar.

18. The method as claimed in claim 1, wherein the reaction time for the first stage of the method is from 5 to 20 hours and for the second stage of the method is 0.5 to 5 hours.

19. The method as claimed in claim 1, wherein the resulting phospholipid of formula (I) is further purified by an alcoholic extraction process.

20. The method as claimed in claim 3, wherein said lecithin is derived from at least one source selected from the group consisting of soybean, rapeseed oil and egg yolks.

21. The method as claimed in claim 16, wherein the immobilized PLD form is covalently bound or adsorptively bound.

22. The method of claim 4, wherein the reaction mixture is in the form of a dispersion.

* * * * *